(12) United States Patent
Kuroda et al.

(10) Patent No.: US 10,143,503 B2
(45) Date of Patent: Dec. 4, 2018

(54) BONE PLATE AND BONE PLATE SYSTEM

(71) Applicant: OLYMPUS TERUMO BIOMATERIALS CORP., Tokyo (JP)

(72) Inventors: Koichi Kuroda, Kanagawa (JP); Mitsuya Urata, Kanagawa (JP); Masaki Yoshida, Saitama (JP)

(73) Assignee: OLYMPUS TERUMO BIOMATERIALS CORP., Tokyo (JP)

( * ) Notice: Subject to any disclaimer, the term of this patent is extended or adjusted under 35 U.S.C. 154(b) by 0 days.

(21) Appl. No.: 15/271,530

(22) Filed: Sep. 21, 2016

(65) Prior Publication Data

US 2017/0007304 A1 Jan. 12, 2017

Related U.S. Application Data

(63) Continuation of application No. PCT/JP2015/058633, filed on Mar. 20, 2015.

(Continued)

(51) Int. Cl.
*A61B 17/80* (2006.01)
*A61B 17/86* (2006.01)

(52) U.S. Cl.
CPC ...... *A61B 17/8057* (2013.01); *A61B 17/8061* (2013.01); *A61B 17/8095* (2013.01); *A61B 17/863* (2013.01)

(58) Field of Classification Search
CPC ............ A61B 17/8019; A61B 17/8028; A61B 17/8061; A61B 17/8095

(Continued)

(56) References Cited

U.S. PATENT DOCUMENTS 4,800,874 A * 1/1989 David ................ A61B 17/8061
606/286
5,938,664 A * 8/1999 Winquist ........... A61B 17/8085
606/283

(Continued)

FOREIGN PATENT DOCUMENTS

AU 2008/353332 B2 10/2009
EP 0 947 176 A2 10/1999

(Continued)

OTHER PUBLICATIONS

International Search Report dated Jun. 23, 2015 issued in PCT/JP2015/058633.

(Continued)

*Primary Examiner* — Matthew Lawson
(74) *Attorney, Agent, or Firm* — Scully, Scott, Murphy & Presser, P.C.

(57) ABSTRACT

A bone plate is provided with: a strip-shaped main-body portion that is secured, along a longitudinal direction of a tibia, to an oblique anterior inner surface of the tibia below a cut formed in an inner surface of the tibia; a transverse portion that is secured to an inner surface of the tibia above the cut along a direction that intersects the longitudinal direction of the tibia; and a joining portion that joins the main-body portion and the transverse portion, wherein the transverse portion and the main-body portion are provided with a plurality of screw holes that are arrayed with spaces between each other and that pass therethrough in plate-thickness directions.

7 Claims, 12 Drawing Sheets

Related U.S. Application Data

(60) Provisional application No. 61/970,445, filed on Mar. 26, 2014.

(58) Field of Classification Search
USPC .................................. 606/280–299, 304
See application file for complete search history.

(56) References Cited

U.S. PATENT DOCUMENTS

| | | |
|---|---|---|
| 6,623,486 B1 | 9/2003 | Weaver et al. |
| 2002/0013587 A1 | 1/2002 | Winquist et al. |
| 2002/0065516 A1 | 5/2002 | Winquist et al. |
| 2003/0199875 A1* | 10/2003 | Mingozzi ........... A61B 17/8095 606/297 |
| 2004/0059334 A1 | 3/2004 | Weaver et al. |
| 2004/0059335 A1 | 3/2004 | Weaver et al. |
| 2004/0186477 A1 | 9/2004 | Winquist et al. |
| 2005/0010226 A1* | 1/2005 | Grady, Jr. ........... A61B 17/746 606/281 |
| 2005/0080421 A1 | 4/2005 | Weaver et al. |
| 2006/0004362 A1* | 1/2006 | Patterson ........... A61B 17/8057 606/291 |
| 2006/0173458 A1 | 8/2006 | Forstein et al. |
| 2007/0162015 A1 | 7/2007 | Winquist et al. |
| 2007/0233106 A1 | 10/2007 | Horan et al. |
| 2008/0132960 A1 | 6/2008 | Weaver et al. |
| 2008/0300637 A1 | 12/2008 | Austin et al. |
| 2009/0143825 A1* | 6/2009 | Graham ............. A61B 17/8014 606/286 |
| 2009/0177203 A1* | 7/2009 | Reiley ................ A61B 17/8095 606/87 |
| 2009/0248084 A1 | 10/2009 | Hintermann |
| 2010/0016858 A1 | 1/2010 | Michel |
| 2010/0030277 A1* | 2/2010 | Haidukewych .... A61B 17/8061 606/286 |
| 2011/0301655 A1* | 12/2011 | Price ................. A61B 17/1728 606/86 R |
| 2013/0172943 A1 | 7/2013 | Austin et al. |
| 2013/0211463 A1* | 8/2013 | Mizuno ............. A61B 17/8095 606/291 |
| 2014/0121710 A1 | 5/2014 | Weaver et al. |
| 2015/0066095 A1* | 3/2015 | Austin ................ A61B 17/74 606/291 |
| 2015/0282851 A1 | 10/2015 | Michel |
| 2016/0074081 A1 | 3/2016 | Weaver et al. |

FOREIGN PATENT DOCUMENTS

| | | | |
|---|---|---|---|
| EP | 1 308 135 A2 | 5/2003 | |
| EP | 2 147 647 A1 | 1/2010 | |
| FR | 2 472 373 A1 | 7/1981 | |
| FR | 2 980 967 A1 | 4/2013 | |
| JP | 2003-509107 A | 3/2003 | |
| JP | 3124178 U | 8/2006 | |
| JP | 2007-500069 A | 1/2007 | |
| JP | 2009-527328 A | 7/2009 | |
| JP | 2010-119638 A | 6/2010 | |
| JP | 2010-220762 A | 10/2010 | |
| JP | 2011-515172 A | 5/2011 | |
| JP | WO2012042592 * | 4/2012 | ......... A61B 17/8095 |
| JP | 2012-165976 A | 9/2012 | |
| JP | 5230697 B2 | 7/2013 | |
| JP | 2014-050722 A | 3/2014 | |
| KR | 30-0743077 | 5/2014 | |
| KR | 30-0743078 | 5/2014 | |
| WO | 01/19267 A1 | 3/2001 | |
| WO | WO 2004/107957 A2 | 12/2004 | |
| WO | WO 2007/100513 A2 | 9/2007 | |

OTHER PUBLICATIONS

Singapore Office Action dated Jan. 4, 2018 in Singapore Patent Application No. 11201607425Y.

Japanese Office Action dated Aug. 22, 2017 in Japanese Patent Application No. 2016-510314.

Extended Supplementary European Search Report dated Nov. 6, 2017 in European Patent Application No. 15 76 9589.1.

Korean Office Action dated Aug. 22, 2017 in Korean Patent Application No. 10-2016-7025048.

* cited by examiner

BONE PLATE AND BONE PLATE SYSTEM

CROSS-REFERENCE TO RELATED APPLICATIONS

This is a continuation of International Application PCT/JP2015/058633, with an international filing date of May 20, 2015, which is hereby incorporated by reference herein in its entirety.

This application is based on U.S. Design Pat. Application No. 61/970,445, filed on Mar. 26, 2014, the contents of which are incorporated herein by reference.

TECHNICAL FIELD

The present invention relates to a bone plate and a bone plate system.

BACKGROUND ART

As a bone plate that secures portions of a broken long bone, including the femur or tibia, there is a known strip-shaped bone plate that has screw holes that are fastened to male screws provided at head portions of a plurality of screws that are fastened to the long bone (for example, see Patent Literature 1).

In the case in which the bone plate of Patent Literature 1 is used in high tibial osteotomy of knee osteoarthritis, a cut made on an inner surface of the tibia is opened; a wedge-shaped artificial bone is inserted thereinto; the bone plate is placed at an anterior inner position of the tibia so as to bridge the cut and so as to avoid soft tissue connected to the tibia, such as medial collateral ligament or the like; and the bone plate is secured to the tibia by means of screws on either side of the cut. At this time, the two portions separated by the cut are supported at three points, namely, a hinge portion positioned on an outer side of the tibia, the artificial bone positioned rearward on an inner side, and the bone plate positioned at the anterior inner side.

CITATION LIST

Patent Literature

{PTL 1} Publication of Japanese Patent No. 5230697

SUMMARY OF INVENTION

Technical Problem

With the bone plate of Patent Literature 1, because a longitudinally long portion that is secured to an oblique anterior inner surface of the tibia below the cut along the longitudinal direction of the tibia and a transverse portion that is secured to an oblique anterior inner surface of the tibia above the cut are placed along substantially the same plane, there is a case of the bone plate is bent so as to lean rearward when a vertical load is exerted to the joint in an upright state.

The present invention is a bone plate and a bone plate system with which it is possible to prevent dislodging of an artificial bone and an increase in retroversion angle of a joint surface, even if a vertical load is exerted on a joint in an upright state after surgery.

Solution to Problem

An aspect of the present invention is a bone plate including: a strip-shaped main-body portion that is secured, along a longitudinal direction of a tibia, to an oblique anterior inner surface of the tibia below a cut formed in an inner surface of the tibia; a transverse portion that is secured to an inner surface of the tibia above the cut along a direction that intersects the longitudinal direction of the tibia; and a joining portion that joins the main-body portion and the transverse portion, wherein the transverse portion and the main-body portion are provided with a plurality of screw holes that are arrayed with spaces between each other and that pass therethrough in plate-thickness directions.

In the above-described aspect, the main-body portion, the joining portion, and the transverse portion may have a continuous curved-surface shape so as to be twisted about an axis parallel to the longitudinal axis of the main-body portion.

In addition, another aspect of the present invention is a bone plate system including: any one of the above-described bone plates; and screws that have head portions including first male screws to be fastened to the screw holes of the bone plate, that have threaded portions including second male screws to be fastened to the tibia, and that secure the bone plate to the tibia.

In the above-described aspect, the screws to be fastened to the screw holes provided in the main-body portion may be fastened in an oblique lateral direction from an oblique anterior inner side of the tibia toward an oblique posterior outer side thereof, and the screws to be fastened to the screw holes provided in the transverse portion may be fastened nearly in the lateral direction from the inner surface of the tibia toward an outer surface thereof.

In addition, in the above-described aspect, when projected onto a joint surface of the tibia, the screws to be fastened to the screw holes provided in the main-body portion and the screws to be fastened to the screw holes provided in the transverse portion may intersect each other in an area that occupies 50% to 80% of the total length of the tibia from the inner surface to the joint surface.

In addition, in the above-described aspect, the screws may be hollow screws having through-holes through which guide pins can pass.

Because the main-body portion and the transverse portion are placed in a twisted manner, the fastening directions of the screws are not uniform, and thus, the securing directions of the screws tend to be mistaken even if preparation holes are provided.

In addition, the above-described aspect may be provided with a wedge-shaped artificial bone member that is inserted into the cut, wherein top and bottom surfaces of the artificial bone member that come into contact with cut surfaces of the cut may be inclined in one direction in the width direction so that the thickness of the artificial bone member gradually decreases.

By doing so, it is possible to facilitate making the top and bottom surfaces of the artificial bone member fit with the cut surfaces of the cut in the tibia.

DESCRIPTION OF EMBODIMENT

A bone plate 1 and a bone plate system 2 according to an embodiment of the present invention will be described below with reference to the drawings.

Figure 1:
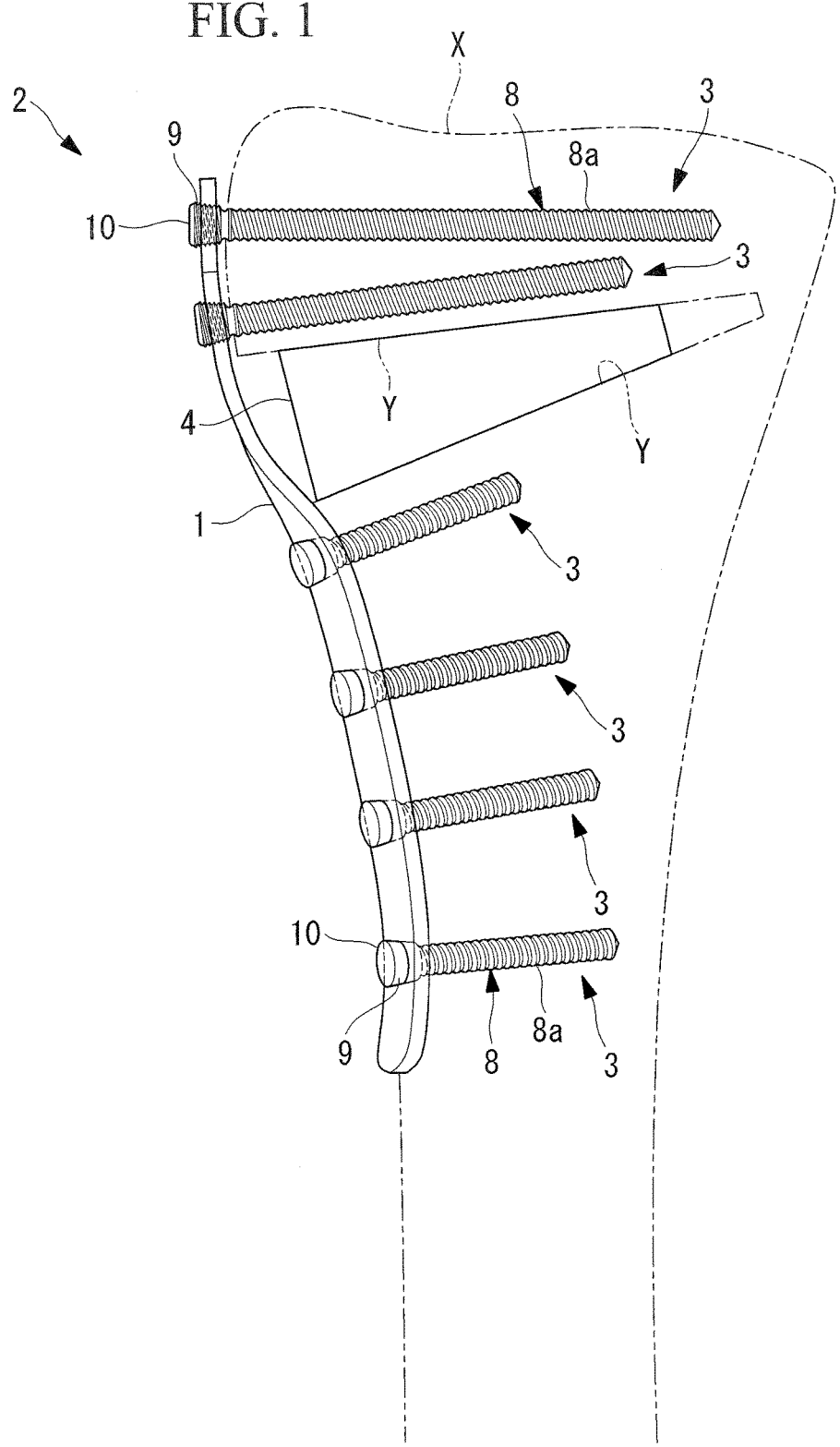
FIG. 1 is a diagram showing the entirety of a bone plate system according to an embodiment of the present invention.

As shown in FIG. 1, the bone plate system 2 according to this embodiment is provided with: the bone plate 1; a plurality of screws 3 for securing the bone plate 1 to an upper side surface of a tibia X; and an artificial bone 4 that is inserted into a cut formed outward in the tibia X from an inner-surface side thereof.

The bone plate 1 according to this embodiment is a long, thin strip-shaped member that is secured to an upper side surface of the tibia X after performing osteotomy in high tibial osteotomy of knee osteoarthritis, and has a subtle curved shape in accordance with the typical surface shape so that the bone plate 1 can be made to conform to the curved surface shape of a side surface of the tibia X at a position at which the shaft portion of the tibia X shifts toward an end portion thereof.

Figure 2A:
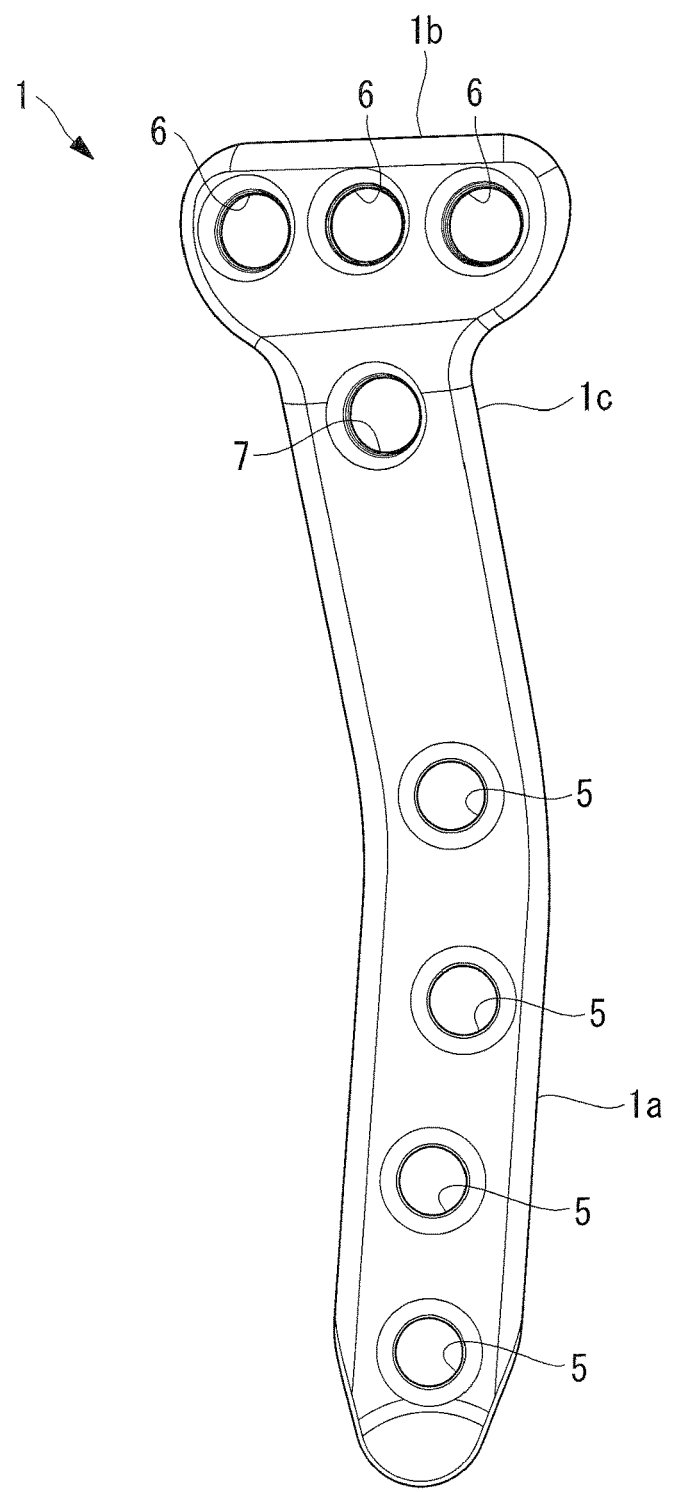
FIG. 2A is a front view showing a bone plate according to the embodiment of the present invention, which is to be used in the bone plate system in FIG. 1.
Figure 2B:
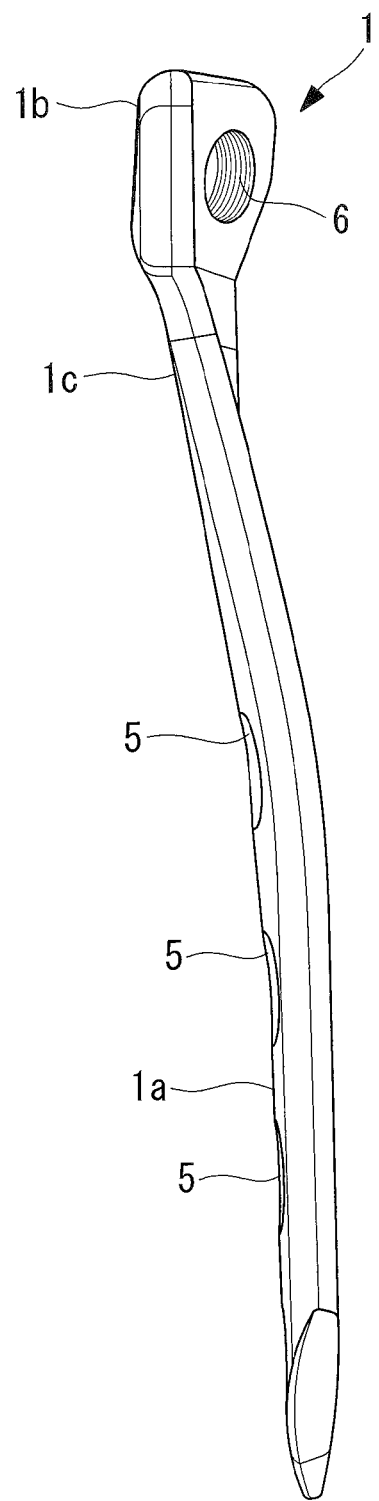
FIG. 2B is a side view showing the bone plate in FIG. 2A.
Figure 2C:
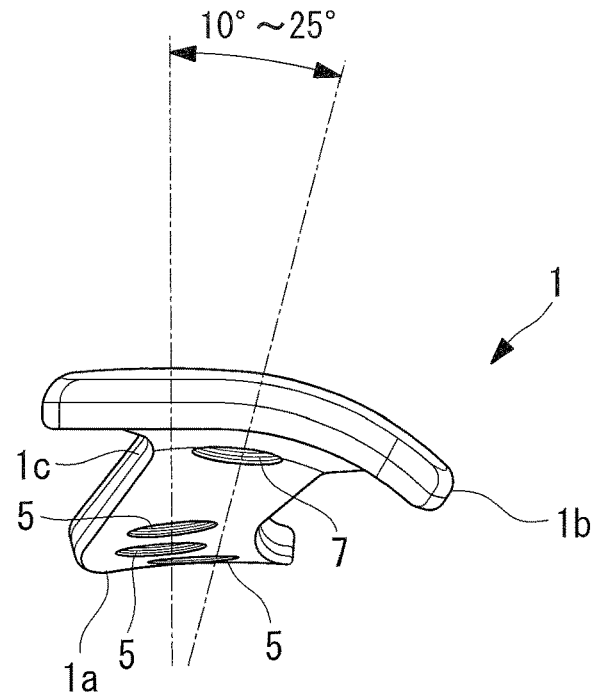
FIG. 2C is a plan view showing the bone plate in FIG. 2A.

As shown in FIGS. 2A, 2B, and 2C, this bone plate 1 is formed in substantially a T-shape as a whole and is provided with: a long, thin strip-shaped main-body portion 1a; a transverse portion 1b that extends in a direction that intersects the longitudinal direction of the main-body portion 1a; and a joining portion 1c that joins the main-body portion 1a and the transverse portion 1b. The joining portion 1c is bent in one direction from one end of the main-body portion 1a and has a twisted shape (with a twist angle of 10° to 25°) about the longitudinal axis of the main-body portion 1a toward the transverse portion 1b at the tip thereof. By doing so, the joining portion 1c is arranged so that the main-body portion 1a and the transverse portion 1b can be made parallel to planes that intersect each other.

The main-body portion 1a of the bone plate 1 is provided with a plurality of screw holes 5 with spaces therebetween in the longitudinal direction thereof. In addition, the transverse portion 1b is provided with a plurality of, for example, three, screw holes 6 with spaces therebetween in a direction that intersects the longitudinal direction of the main-body portion 1a and one screw hole 7 with spaces relative to the screw holes 5 and 6 in the aforementioned longitudinal direction.

Figure 3:
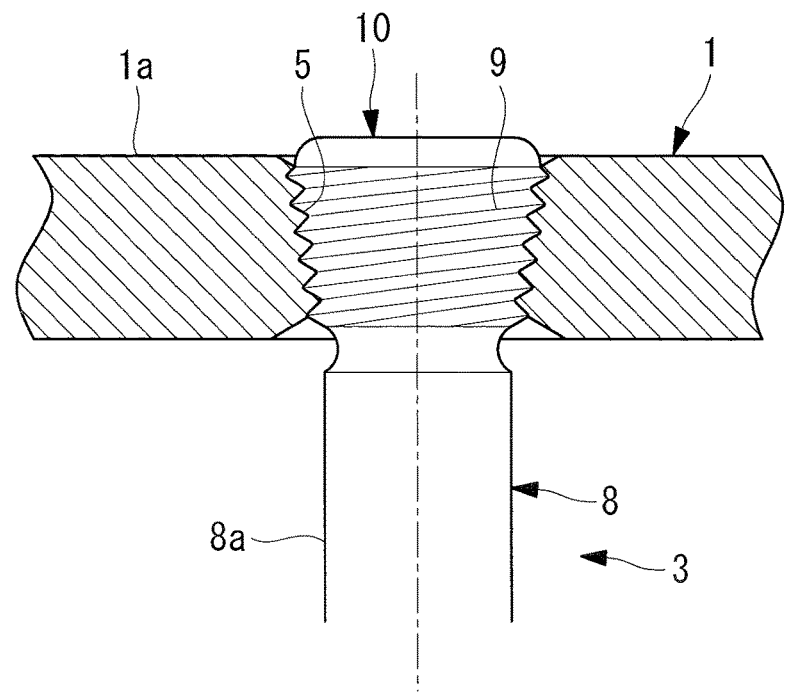
FIG. 3 is a partial longitudinal cross-sectional view showing the relationship between screws and screw holes provided in the bone plate in FIG. 2A.

As shown in FIG. 3, these screw holes 5, 6, and 7 are tapered screw holes and have inner diameters that gradually decrease from one side to the other side in the plate-thickness direction, that is, toward the side that is made to face the tibia X. Note that, although the case of the screw hole 5 of the main-body portion 1a is shown as an example in FIG. 3, the configurations of the screw holes 6 and 7 of the transverse portion 1b and the joining portion 1c are the same.

As shown in FIGS. 1 and 3, the screws 3 are formed in long, thin circular-rod shapes and are provided with threaded portions 8 that have, on the outer circumferential surfaces thereof, bone-securing male threaded portions (second male screws) 8a to be fastened to preparation holes (not shown) formed in the tibia X and head portions 10 provided with tapered screws (first male screws) 9 to be fastened to the screw holes 5, 6, and 7 of the bone plate 1.

Figure 4:
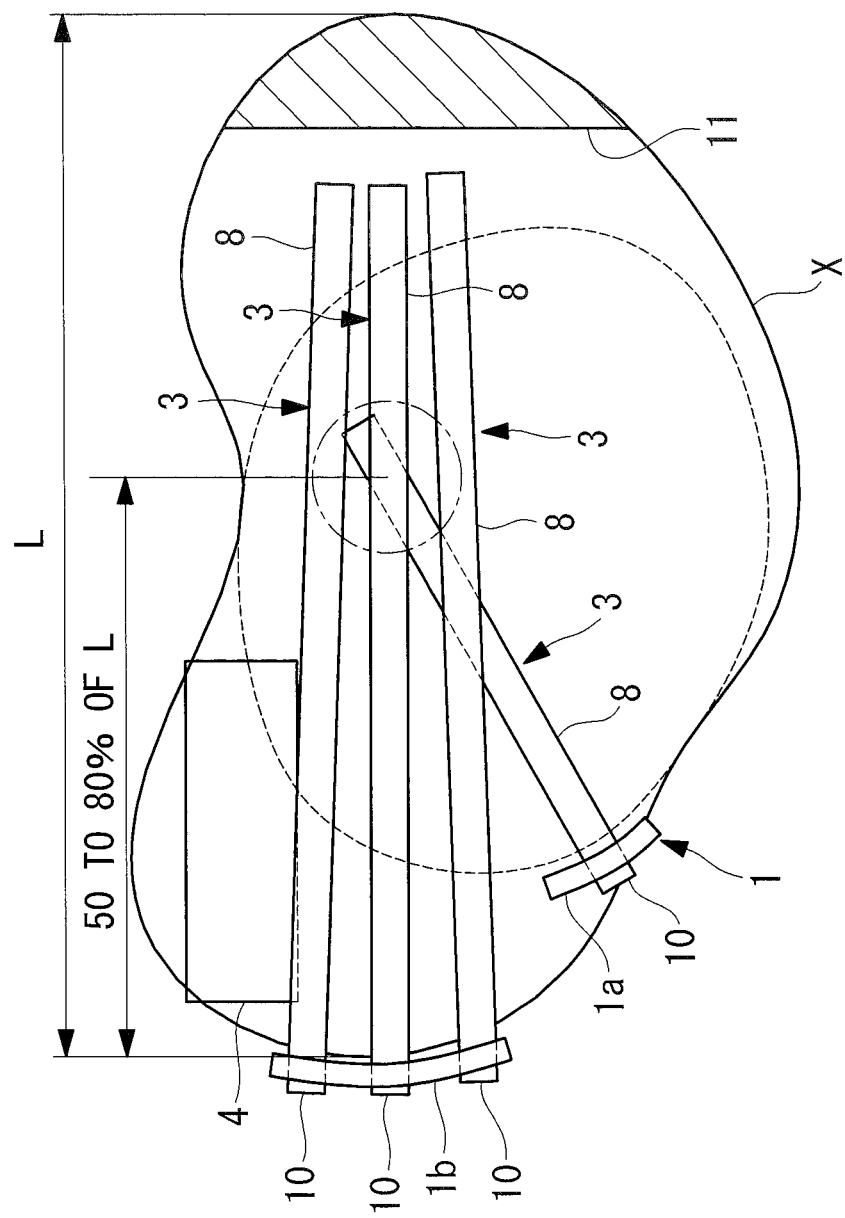
FIG. 4 is a diagram in which the arrangement of the screws in the bone plate system in FIG. 1 is projected onto a joint surface.

Because the main-body portion 1a and the transverse portion 1b are placed at mutually twisted positions when the tapered screws 9 of the head portions 10 of the screws 3 are fastened to the screw holes 5 formed in the main-body portion 1a of the bone plate 1 and the screw holes 6 formed in the transverse portion 1b thereof, as shown in FIG. 4, the screws 3, when projected onto the joint surface, are configured to be fastened so as to intersect each other. These intersecting positions of the screws 3 are placed in an area occupying 50% to 80% of the total width of the tibia X from the inner surface to the joint surface in the lateral direction.

Figure 5:
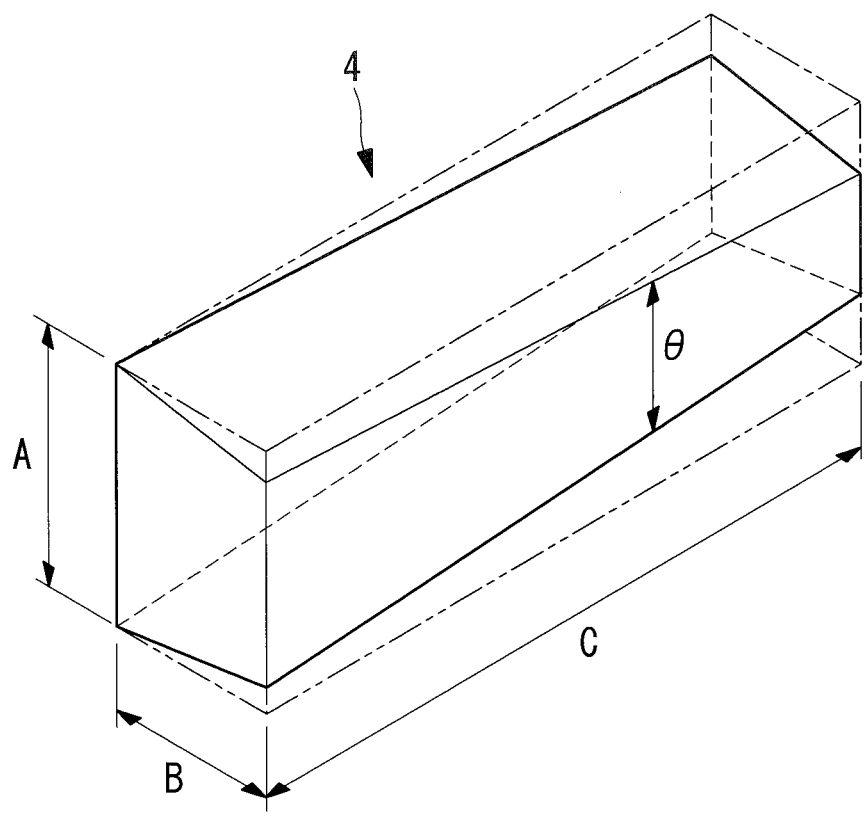
FIG. 5 is a perspective view showing an example artificial bone to be used in the bone plate system in FIG. 1.

As shown in FIG. 5, the artificial bone 4 is formed of a calcium-phosphate-based ceramic and is formed in substantially a wedge-like block shape. More specifically, in the artificial bone 4, at least one of the surfaces (top and bottom surfaces) that come into contact with cut surfaces Y of the tibia X when inserted into the cut is formed of an inclined surface in which the thickness thereof gradually decreases along one direction in the longitudinal direction and one direction in the width direction. FIG. 5 shows an example in which the top and bottom surfaces are both formed of the inclined surfaces.

The operation of the thus-configured bone plate 1 and bone plate system 2 according to this embodiment will be described below.

In order to perform high tibial osteotomy of knee osteoarthritis by using the bone plate system 2 according to this embodiment, a cut is formed outward from an inner surface of the tibia X in a direction inclined with respect to the longitudinal axis of the tibia X, and the cut surfaces Y are separated by using predetermined equipment. Then, as shown in FIG. 1, when the main-body portion 1a of the bone plate 1 is placed at an oblique anterior inner surface of the tibia X in the state in which the wedge-shaped artificial bone 4 is inserted between the separated cut surfaces Y, because the joining portion 1c bridges the cut and the transverse portion 1b is placed at a joint-surface-side inner surface of the tibia X, the preparation holes are formed inside the individual screw holes 5, 6, and 7 of the main-body portion 1a and the transverse portion 1b.

At this time, the preparation holes are formed along the axial directions of the individual screw holes 5, 6, and 7. Then, the male threaded portions 8a of the screws 3 are fastened to the preparation holes after being made to pass through the individual screw holes 5, 6, and 7, and, finally, the tapered screws 9 provided in the head portions 10 of the screws 3 are fastened to the screw holes 5, 6, and 7.

By doing so, the bone plate 1 is secured to the tibia X in a state in which the bone plate 1 is placed along the surface of the tibia X. Because the individual screw holes 5, 6, and 7 and the first male screws 9 of the head portions 10 of the screws 3 are formed of the tapered screws, securing forces are increased as fastening proceeds, and thus, it is possible to more reliably secure the bone plate 1 to the surface of the tibia X.

Then, the wedge-shaped artificial bone 4 is subsequently inserted into the cut. By doing so, a vertical load exerted in the direction that closes the cut can be supported by the tibia X above and below the opened cut at three points, namely, at a hinge portion 11 provided on the outside, the bone plate 1 secured from the oblique anterior inner surface to the inner surface, bridging the cut, and the artificial bone 4 sandwiched between the cut surfaces Y.

In this case, with the bone plate 1 according to this embodiment, the main-body portion 1*a* and the transverse portion 1*b* that are secured to the tibia X, bridging the cut, are placed at mutually twisted positions by the joining portion 1*c*, and thus, the main-body portion 1*a* is secured to the oblique anterior inner surface of the tibia X, whereas the transverse portion 1*b* is secured to the inner surface of the tibia X. As a result, even if a vertical load acts on the tibia X from the femur via the joint surface of a patient standing upright after surgery, it is possible to prevent the vertical load from generating a moment that bends the bone plate 1 in the plate-thickness direction.

In other words, with a conventional bone plate 12 in which the main-body portion 1*a* and the transverse portion 1*b* are placed on substantially the same plane, a vertical load generates a moment that bends the bone plate 12 in the plate-thickness direction when the vertical load acts on the joint surface. As a result, there is a problem in that, when the bone plate 12 is bent in the plate-thickness direction, the artificial bone 4 is expelled (dislodged) from the cut, which closes the opened cut, and thus, the joint surface is inclined rearward (retroverted) and the bone is healed in this state.

In contrast, with the bone plate 1 according to this embodiment, by twisting the joining portion 1*c*, because the vertical load acts between the bone plate 1 and the hinge portion 11 and is reliably received by the two points on both sides, a moment that bends the bone plate 1 in the plate-thickness direction is not generated, and thus, it is possible to more reliably prevent dislodging of the artificial bone 4 and retroversion of the joint surface.

In addition, although it is possible to achieve the same effects so long as the main-body portion 1*a* can be secured to the inner surface of the tibia X, because soft tissue, such as the medial collateral ligament or the like, is connected to the tibia X below the cut, it is not possible to secure the main-body portion 1*a* to the inner surface of the tibia X.

By securing the main-body portion 1*a* to the oblique anterior inner surface of the tibia X and by securing only the transverse portion 1*b* to the inner surface of the tibia X by twisting the joining portion 1*c*, there is an advantage in that it is possible to more reliably prevent dislodging of the artificial bone 4 and retroversion of the joint surface while avoiding the soft tissue, such as medial collateral ligament or the like.

Figure 6:
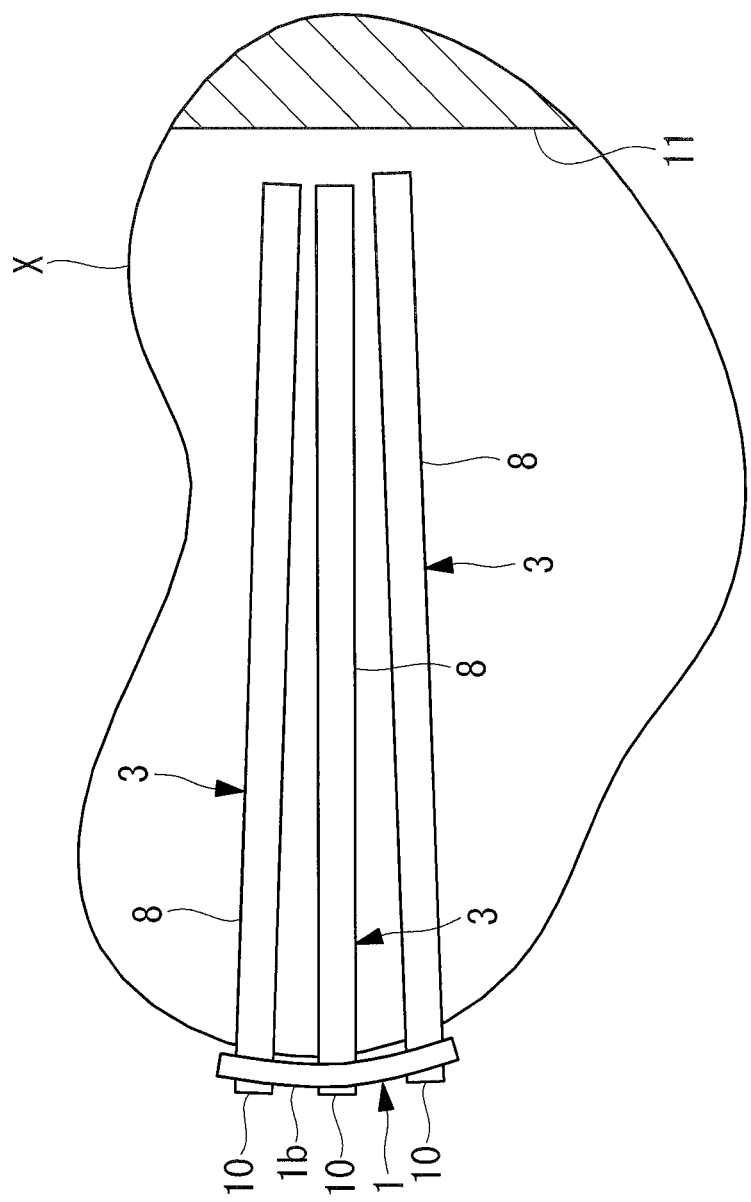
FIG. 6 is a diagram showing the arrangement of the screws secured to a transverse portion of the bone plate in the bone plate system in FIG. 1.
Figure 7:
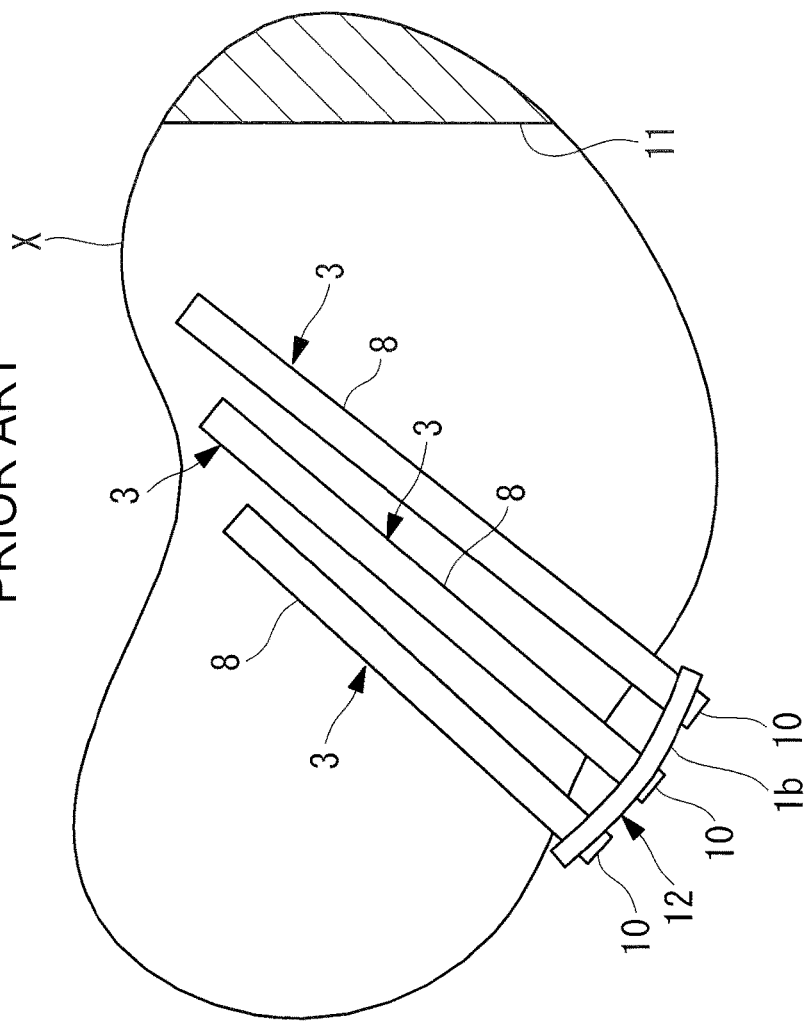
FIG. 7 is a diagram showing the arrangement of screws in a conventional bone plate system shown as a comparative example for FIG. 6.

In addition, by placing the transverse portion 1*b* at the inner surface of the tibia X, the screws 3 to be secured to the transverse portion 1*b* are fastened so as to move laterally straight toward the hinge portion 11 across the tibia X on the joint-surface side, as shown in FIG. 6. In the related art, as shown in FIG. 7, when placing the transverse portion 1*b* at an oblique anterior inner surface, because the screws 3 are fastened to the tibia X in the direction of the oblique posterior outer side, the use of the screws 3 has been limited to short ones. With this embodiment, long screws 3 can be fastened to the tibia X in the portions thereof having long dimensions so as to move laterally straight thereacross. In general, in the case in which the bone quality is poor, using the short screws 3 under unsatisfactory securing conditions causes the screws 3 to move in the cancellous bone, which sometimes cut the cancellous bone; however, by using the long screws 3, there is an advantage in that it is possible to maintain the cancellous bone in a healthy state.

In addition, with the bone plate system 2 according to this embodiment, the screws 3 can be fastened in the oblique posterior direction with the main-body portion 1*a* placed at the oblique anterior inner surface of the tibia X, and the screws 3 can be fastened straight in the horizontal direction with the transverse portion 1*b* placed at the inner surface of the tibia X.

According to FIG. 4, the screws 3, when projected onto the joint surface of the tibia X, intersect each other in an area occupying 50% to 80% of the total width from the inner surface to the joint surface of the tibia X in the lateral direction.

In the state in which the patient is standing upright, the centers of the resultant forces of loads exerted on the joint from the femur are generally placed at positions occupying 60% or more of the total length from the inner surface to the joint surface. Therefore, by aligning the positions at which the screws 3 intersect with the positions of the centers of the resultant forces of the loads, there is an advantage in that it is possible to facilitate capturing of the loads exerted on the tibia X from the femur by using the bone plate 1.

In addition, because the artificial bone 4 is not only formed in a wedge shape in which the size thereof decreases toward the tip in the longitudinal direction but also has an inclined surface in which the thickness thereof decreases in one direction also in the width direction, the bone plate system 2 according to this embodiment affords the following advantages.

Specifically, because the size of the artificial bone 4 decreases toward the tip along the longitudinal direction, by inserting, from the inner-surface side, the wedge-shaped artificial bone 4 into the cut formed in a shape that, by being opened, expands toward an opening end on the inner-surface side, it is possible to bring the top and bottom surfaces of the artificial bone 4 into close contact with the cut surfaces Y above and below.

Figure 8:
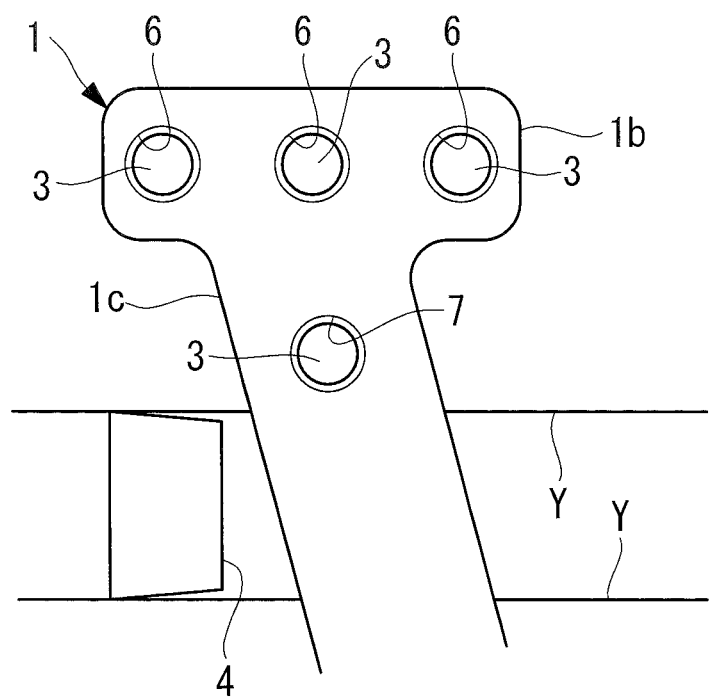
FIG. 8 is a diagram of an artificial bone that is used in the bone plate system in FIG. 1, as viewed from an inner surface side of a tibia.

Furthermore, with the artificial bone 4 in this embodiment, because at least one of the top and bottom surfaces thereof is inclined so that the thickness decreases in one direction also in the width direction, in the state in which the artificial bone 4 is inserted into the cut, it is possible to place the artificial bone 4 so that the thickness thereof becomes large rearward and low forward, as shown in FIG. 8. By doing so, even if a vertical load acts on the tibia X from the femur via the joint surface of a patient standing upright after surgery, it is possible to prevent retroversion of the joint surface, and it is also possible to more reliably bring the top and bottom surfaces of the artificial bone 4 into close contact with both of the cut surfaces Y.

Figure 9:
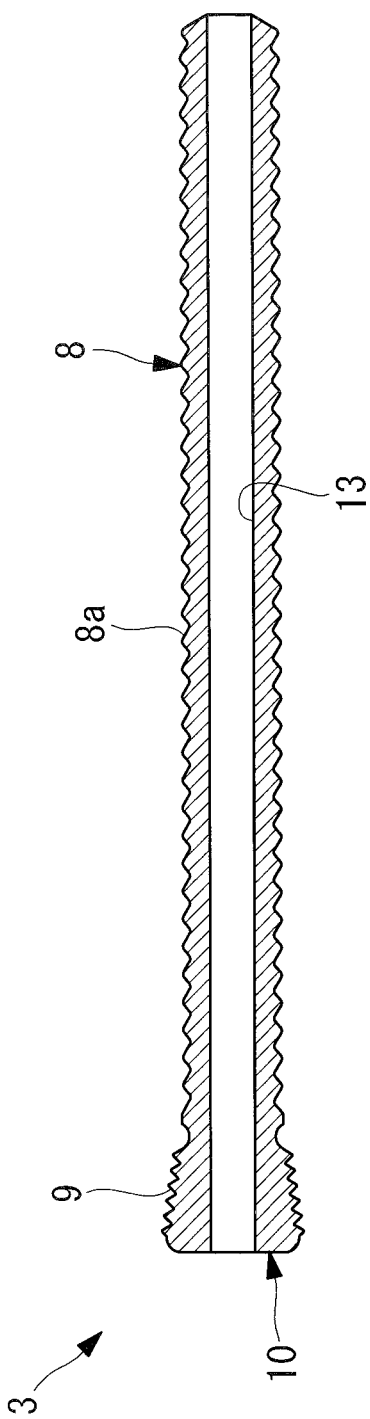
FIG. 9 is a longitudinal cross-sectional view showing screws that are used in a modification of the bone plate system in FIG. 1.

Note that, in this embodiment, as shown in FIG. 9, hollow screws 3 that have through-holes 13 through which guide pins 14 can pass may be employed as the screws 3.

Figure 10:
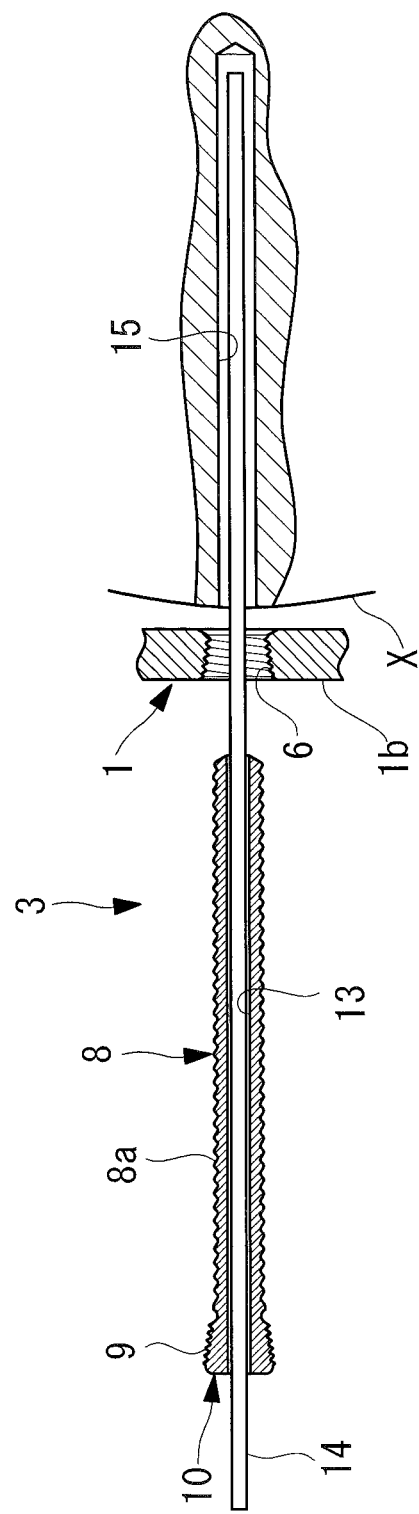
FIG. 10 is a diagram for explaining the procedure for fastening the screws in FIG. 9 by using guide pins.

As shown in FIG. 4, because the main-body portion 1*a* and the transverse portion 1*b* of the bone plate 1 are placed in different planes by twisting the joining portion 1*c*, the fastening directions of the screws 3 are not uniform, and thus, the securing directions of the screws 3 are easily mistaken even if preparation holes are provided in the tibia X. By doing so, there is an advantage in that, as shown in FIG. 10, by utilizing the through-holes 13 provided in the screws 3, it is possible to fasten the screws 3 by using the guide pins 14 inserted into preparation holes 15 in advance as guides, and thus, it is possible to enhance the workability of the fastening procedure.

In addition, in this embodiment, as shown in FIG. 5, it is preferable that the dimensions of the wedge-shaped artificial bone 4 be set as below:

$|\theta|-|A|\pm 1.5$, $5 \leq A \leq 20$ mm, $5 \leq B \leq 20$ mm, and $10 \leq C \leq 50$ mm, where θ is the angle at the tip of the wedge shape in the artificial bone 4, A is the maximum height of the artificial bone 4, B is the width of the artificial bone 4, and C is the length of the artificial bone 4. By configuring the artificial bone to have such dimensions, it is possible to provide a wedge shape having the dimensions that fit the dimensions of the human tibia X.

It is more preferable that the dimensions be:

$|\theta| \approx |A|$, $6 \leq A \leq 15$ mm, $8 \leq B \leq 15$ mm, and $25 \leq C \leq 50$ mm.

In addition, it is preferable that the artificial bone 4 be formed of a calcium-phosphate-based ceramic having a porosity of 30% to 80%. Examples thereof include βTCP, αTCP, OCP, hydoroxyapatite, bio-derived materials, calcium sulfate cement, and so forth.

Figure 11:
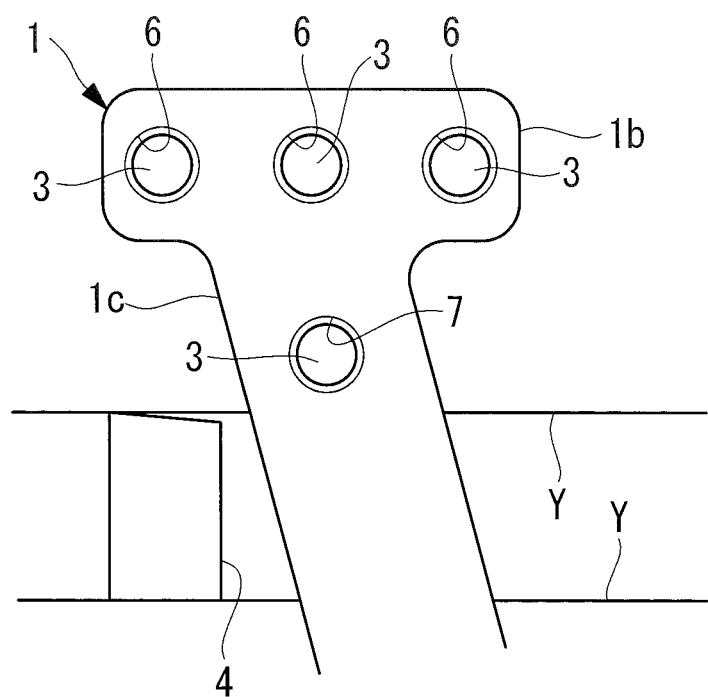
FIG. 11 is a diagram showing a modification of the artificial bone in FIG. 8.

In addition, in this embodiment, although the artificial bone 4 has inclined surfaces both in the top and bottom surfaces thereof, alternatively, as shown in FIG. 11, only the top surface or the bottom surface may be formed as an inclined surface.

As mentioned above, by the bone plate of the present invention, when the strip-shaped main-body portion is placed, along the longitudinal direction of the tibia, at the oblique anterior inner surface of the tibia below the cut formed in the inner surface of the tibia, the transverse portion is placed at a position extending along the inner surface of the tibia above the cut. It is possible to hold the opened cut by individually securing the main-body portion and the transverse portion to the tibia on either side of the cut by using the screws fastened to the screw holes.

In this case, because the main-body portion and the transverse portion that are joined by the joining portion are respectively secured to the oblique anterior inner surface and the inner surface of the tibia in a twisted manner, it is possible to prevent the bone plate from bending and collapsing, even if a vertical load is exerted to the joint in an upright state, as does happen with a conventional bone plate that is secured along substantially the same plane. As a result, it is possible to prevent dislodging of the artificial bone that is inserted into the cut and bone healing in a retroverted state.

When the bone plate is placed at a side surface of the tibia, the bone plate is placed so as to conform to the side-surface shape of the tibia, and thus, the bone plate does not become a hindrance by greatly protruding when subcutaneously implanted.

The bone plate is placed at an upper side surface of the tibia; the screws are individually made to pass through the plurality of screw holes that are provided in the main-body portion and the transverse portion, respectively; the threaded portions having the second male screws are fastened to the tibia; and, finally, the head portions having the first male screws are fastened to the screw holes; and thus, it is possible to hold the cut in an open state by reliably securing the bone plate to the tibia on either side of the cut.

The screws are fastened to the tibia closer to the joint surface located above the cut in nearly the lateral direction toward the outer surface from the inner surface of the tibia by utilizing the screw holes of the transverse portion placed at the inner surface. In the case of the related art in which a bone plate is secured to an oblique anterior inner surface of the tibia, screws must be diagonally fastened toward the oblique posterior outer surface from the oblique anterior inner surface, and, in the case in which the bone quality is poor, it is not only impossible to achieve sufficient securing forces but the screws also move in the cancellous bone in some cases, thus cutting the cancellous bone. As compared with this, by fastening the screws nearly in the lateral direction in which the lateral cross-sectional dimension of the tibia is large, it is possible to employ longer screws, and thus, it is possible to maintain the health of the cancellous bone by achieving high securing forces.

When loads from the femur are exerted on the joint in an upright state after surgery, the centers of resultant forces of the loads projected onto the joint surface of the tibia are generally placed at positions occupying 60% or more of the total length of the tibia from the inner surface to the joint surface. Doing so facilitates capturing of the loads exerted on the tibia from the femur by using the bone plate.

Because the main-body portion and the transverse portion are placed in a twisted manner, the fastening directions of the screws are not uniform, and thus, the securing directions of the screws tend to be mistaken even if preparation holes are provided.

By utilizing the through-holes provided in the screws, it is possible to fasten the screws by using the guide pins inserted into preparation holes in advance as guides, and thus, it is possible to enhance the workability of the fastening procedure.

It is possible to facilitate making the top and bottom surfaces of the artificial bone member fit with the cut surfaces of the cut in the tibia.

REFERENCE SIGNS LIST

1, 12 bone plate
1*a* main-body portion
1*b* transverse portion
1*c* joining portion
2 bone plate system
3 screw
4 artificial bone (artificial bone member)
5, 6, 7 screw hole
8 threaded portion
8*a* male threaded portion (second male screw)
9 tapered screw (first male screw)
10 head portion
13 through-hole
14 guide pin
X tibia

The invention claimed is:

1. A bone plate comprising:
   a strip-shaped main-body portion that is configured to be secured, along a longitudinal direction of a tibia, to an oblique anterior inner surface of the tibia below a cut formed in an inner surface of the tibia;
   a transverse portion that is configured to be secured to an inner surface of the tibia above the cut along a direction that intersects the longitudinal direction of the tibia; and
   a joining portion disposed along the longitudinal direction between the main-body portion and the transverse portion to join the main-body portion to the transverse portion,
   wherein the main-body portion, the joining portion, and the transverse portion have a continuous curved-surface shape and the joining portion is twisted relative to a longitudinal axis of the joining portion such that the main-body portion and transverse portion extend on different planes; and
   the transverse portion is elongated in a direction transverse to the longitudinal axis of the joining portion such that a width of the transverse portion is wider than a width of the strip-shaped main body portion and a width of the joining portion.

2. A bone plate system comprising:
   a bone plate according to claim 1; and
   screws that have head portions including first male screws to be fastened to screw holes of the bone plate, that have threaded portions including second male screws to be fastened to the tibia, and that secure the bone plate to the tibia.

3. A bone plate system according to claim 2, wherein the screws to be fastened to the screw holes provided in the main-body portion are fastened in an oblique lateral direction from an oblique anterior inner side of the tibia toward an oblique posterior outer side thereof, and the screws to be fastened to the screw holes provided in the transverse portion are fastened nearly in a lateral direction from the inner surface of the tibia toward an outer surface thereof.

4. A bone plate system according to claim 2, wherein, when projected onto a joint surface of the tibia, the screws include first screws to be fastened to the screw holes provided in the main-body portion and second screws to be fastened to the screw holes provided in the transverse portion, the first and second screws intersecting each other in an area that occupies 50% to 80% of the total length of the tibia from the inner surface to the joint surface.

5. A bone plate system according to claim 2, wherein the screws are hollow screws having through-holes through which guide pins can pass.

6. A bone plate system according to claim 2, further comprising:
   a wedge-shaped artificial bone member that is configured to be inserted into the cut,
   wherein top and bottom surfaces of the artificial bone member that come into contact with cut surfaces of the cut are inclined in one direction in the width direction so that the thickness of the artificial bone member gradually decreases.

7. The bone plate according to claim 1, wherein the transverse portion is twisted relative to the main body portion about an axis parallel to a longitudinal axis of the main-body portion such that a first portion of a plurality of screw holes disposed in the transverse portion are directed in a first direction and a second portion of the plurality of screw holes disposed in the main body portion are directed in a second direction, the first and second directions being offset in a direction transverse to the longitudinal axis of the main-body portion.

* * * * *